United States Patent [19]

Fougret et al.

[11] Patent Number: 6,040,262
[45] Date of Patent: Mar. 21, 2000

[54] CATALYST AND USE THEREOF

[75] Inventors: Christoph Martin Fougret, Falkirk, United Kingdom; Wolfgang Friederich Holderich, Frankenthal, Germany

[73] Assignee: BP Chemicals Limited, London, United Kingdom

[21] Appl. No.: 09/265,567

[22] Filed: Mar. 10, 1999

[30] Foreign Application Priority Data

Mar. 10, 1998 [GB] United Kingdom .................. 9805107

[51] Int. Cl.⁷ ............................ B01J 31/00; B01J 27/14; B01J 27/198; B01J 27/188; B01J 27/19
[52] U.S. Cl. ....................... 502/162; 502/164; 502/208; 502/209; 502/210; 502/211; 502/214
[58] Field of Search ................................... 502/162, 164, 502/208, 209, 210, 211, 214

[56] References Cited

U.S. PATENT DOCUMENTS

| | | | |
|---|---|---|---|
| 2,613,188 | 10/1952 | Mavity | 502/214 |
| 2,876,266 | 3/1959 | Wegner | 502/214 |
| 3,248,341 | 4/1966 | Louvar | 502/214 |
| 3,340,313 | 9/1967 | Mitsutani | 502/214 |
| 3,554,926 | 1/1971 | Statman | 502/214 |
| 3,758,615 | 9/1973 | Izumi et al. | 260/641 |
| 3,862,249 | 1/1975 | Ester et al. | 502/214 |
| 3,917,721 | 11/1975 | Frampton | 502/214 |
| 4,012,452 | 3/1977 | Frampton | 502/214 |
| 4,038,211 | 7/1977 | Frampton | 502/214 |
| 4,528,398 | 7/1985 | Callahan et al. | 502/212 |
| 4,837,192 | 6/1989 | Roberts | 502/211 |
| 4,946,815 | 8/1990 | Chao et al. | 502/214 |
| 5,081,086 | 1/1992 | Wilcher et al. | 502/214 |
| 5,116,796 | 5/1992 | Edlund et al. | 502/164 |
| 5,366,948 | 11/1994 | Kresge et al. | 502/214 |
| 5,681,973 | 10/1997 | Hoelderich et al. | 556/26 |
| 5,714,429 | 2/1998 | Haining | 502/211 |
| 5,792,721 | 8/1998 | Grate et al. | 502/209 |
| 5,817,831 | 10/1998 | Rhubright et al. | 502/117 |
| 5,824,825 | 10/1998 | Lansink-Rotgerink et al. | 502/214 |

FOREIGN PATENT DOCUMENTS

| | | |
|---|---|---|
| 0 002 899 A1 | 7/1979 | European Pat. Off. . |
| 0 704 240 A1 | 4/1996 | European Pat. Off. . |
| 0 771 781 A1 | 5/1997 | European Pat. Off. . |
| 1 564 223 | 4/1980 | United Kingdom . |
| 94/21583 | 9/1994 | WIPO . |

*Primary Examiner*—Mark L. Bell
*Assistant Examiner*—Patricia L. Hailey
*Attorney, Agent, or Firm*—Nixon & Vanderhye

[57] ABSTRACT

The present invention relates to a catalyst composition comprising an acid supported on carrier characterised in that said composition comprises in addition an amino compound.

10 Claims, No Drawings

CATALYST AND USE THEREOF

The present invention relates to a novel catalyst composition comprising an acid supported on a carrier and an amino compound, and the use thereof as a catalyst in a process such as for the hydration of olefins to alcohols.

It is well known to support acid catalysts such as phosphoric acid or heteropolyacids on a carrier such as eg silica or clay and to use such a supported catalyst for the hydration of olefins such as ethylene or propylene in the vapour phase to the corresponding alcohols. Numerous prior art publications describe such a procedure including those disclosed in GB-A-1570650, U.S. Pat No. 4,808,559, GB-A-1371905, U.S. Pat No. 4,038,211, U.S. Pat. No. 4,012,452, GB-A-1476534, GB-A-1306141, U.S. Pat. No. 3,996,338 and CAN-A-844004. In each of these prior publications, the nature of the siliceous support used is defined by various parameters including the pore volume, the surface area, the crush strength and the purity of the support.

Some of the prior art publications such as eg GB-A-1281120 describe a liquid phase process for the hydration of olefins using a heteropolyacid catalyst. Furthermore, U.S. Pat. No. 2,173,187 describes a process for the hydration of olefins in the vapour phase to the corresponding alcohols by using as catalyst heteropolyacid, the complex anion of which includes one element from Group VI, sub-Group A of the Periodic table. It is stated in this reference that the catalyst can be used with or without a support. The supports, when used, are said to be preferably silica gel although other siliceous supports such as silicic acid, Japanese acid clay, bentonite, kieselguhr, or asbestos are also listed. Similarly, JA-A-57130935 describes a process for olefin hydration using a heteropolyacid catalyst supported on activated carbon. Furthermore, U.S Pat. No. 2,608,534 describes a heteropolyacid supported on a major amount of an inorganic metal oxide or hydroxide as catalyst for a number of general organic reactions including inter alia the hydration of olefins. Amongst the supports disclosed in this publication are alumina, magnesia, thoria, titania and the like and alumina is said to be preferred. However, there is no disclosure of any specific catalyst or specific process for the hydration of olefins to the corresponding alcohols.

It has now been found that a supported acid catalyst of improved activity and stability can be formed by using an amino compound in the preparation of such a supported catalyst.

Accordingly, the present invention is a catalyst composition comprising an acid supported on carrier characterised in that said composition comprises in addition an amino compound.

The acid catalyst which may be used in the catalyst composition of the present invention is suitably phosphoric acid or a heteropolyacid. The phosphoric acid can be in any of its isomeric forms, eg ortho-phosphoric acid or meta-phosphoric acid or mixtures thereof. Ortho-phosphoric acid is preferred. The term "heteropolyacids" as used herein and throughout the specification is meant to include the free acids and salts thereof. The heteropolyacids used to prepare the catalysts of the present invention therefore include the free acids and the coordination-type salts thereof in which the anion is a complex, high molecular weight entity. Typically, the anion is comprises 2–18 oxygen-linked polyvalent metal atoms, which are called peripheral atoms. These peripheral atoms surround one or more central atoms in a symmetrical manner. The peripheral atoms are usually one or more of molybdenum, tungsten, vanadium, niobium, tantalum and other metals. The central atoms are usually silicon or phosphorus but can comprise any one of a large variety of atoms from Groups I–VIII in the Periodic Table of elements. These include, for instance, lithium ions, cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hanium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters". The structures of some of the well known anions are named after the original researchers in this field and are known eg as Keggin, Wells-Dawson and Anderson-Evans-Perloff structures.

Heteropolyacids usually have a high molecular weight eg in the range from 700–8500 and include dimeric complexes. They have a relatively high solubility in polar solvents such as water or other oxygenated solvents, especially if they are free acids and in the case of several salts, and their solubility can be controlled by choosing the appropriate counter ions. Specific examples of heteropolyacids that may be used as the catalysts in the present invention include:

1–12-tungstophosphoric acid - $H_3[PW_{12}O_{40}].xH_2O$
1–12-molybdophosphoric acid - $H_3[PMo_{12}O_{40}].xH_2O$
1–12-tungstosilicic acid - $H_4[SiW_{12}O_{40}].xH_2O$
1–12-molybdosilicic acid - $H_4[SiMo_{12}O_{40}].xH_2O$
Potassium tungstophosphate - $K_6[P_2W_{18}O_{62}].xH_2O$
Sodium molybdophosphate - $Na_3[PMo_{12}O_{40}].xH_2O$
Ammonium molybdodiphosphate - $(NH_4)_6[P_2Mo_{18}O_{62}].xH_2O$
Sodium tungstonickelate - $Na_4[NiW_6O_{24}H_6].xH_2O$
Ammonium molybdodicobaltate - $(NH_4)[Co_2Mo_{10}O_{36}].xH_2O$
Cesium hydrogen tungstosilicate - $Cs_3H[SiW_{12}O_{40}].xH_2O$
Potassium molybdodivanado phosphate - $K_5[PMoV_2O_{40}].xH_2O$
Copper hydrogen tungstosilicate - $CuH_2[SiW_{12}O_{40}].xH_2O$
Lithium hydrogen tungstosilicate - $Li_3H[SiW_{12}O_{40}].xH_2O$ The carrier on which the acid catalyst is supported is suitably one or more of siliceous supports, clays, titania, zirconia, hafnia, carbon and the like, and is preferably a silica support. The support may be in the form of gels, extrudates, pellets or granules and may be either a natural product or can be produced synthetically. This is particularly the case with silicas which may be synthetic silicas produced eg by the flame hydrolyis of silicon tetrachloride. Examples of such silicas include those commercially sold as the Grace/Davison grades of silica especially Grace 57 and 1371 silicas (ex W R Grace), and the Aerosil grades of silicas (ex Degussa) such as those claimed and described in U.S. Pat. No. 5,086,031. The supports, especially the silica supports, suitably have the following characteristics:

Pore radius (prior to use) of 10–500 Å, preferably 30–100 Å

Bulk density of 0.3–0.45 g/ml, preferably 0.38–0.42 g/ml

Pore volume (water) of 0.40–1.25 ml/g, preferably 0.90–1.20 ml/g

Surface area of 200–750 m²/g, preferably 250–450 m²/g

Average particle size of 0.1–6.0 mm, preferably 1–3.5 mm.

Within the above ranges, where a used silica is employed as carrier/support for the acid, such silica may have an increased surface area compared to a fresh, unused silica and this increased surface area may be closer to the upper limit of the specified range.

It has now been found that by incorporating an amino compound into the catalyst composition during the preparation thereof, the activity and stability thereof can be improved. Thus, it is possible to treat the support initially with an amino compound or to pre-mix the amino compound with the acid catalyst before immersing the support into the catalyst solution. Alternatively, it would be possible to incorporate the amino compound into the catalyst by co-feeding the amino compound and the catalyst solution on to a support to be impregnated.

The amino compound used is suitably non-ionic or cat-ionic and may be respectively the free amine or a salt thereof. The amino compound is suitably (a) saturated or unsaturated, (b) open chain, cyclic, alicyclic or exo-cyclic and (c) aliphatic, aromatic or heterocyclic and may be a primary, secondary or a tertiary amine which may in turn be a mono- di- or polyalkylene polyamine. In particular, where the amine is an alkyl or an aryl amine, it suitably has from 1–10 carbon atoms and is suitably dimethyl amine, trimethyl amine, a polyalkylene polyamine or ammonium salts thereof including the hydroxides and halides such as eg chlorides and bromides.

The support or carrier is suitably impregnated with a solution of the catalyst and the amino compound which is prepared in turn by dissolving the catalyst and the amino compound in a solvent such as eg an alcohol or distilled water. The support is then added to the solution so formed. The support is suitably left to soak in the solution of the catalyst and the amino compound for a duration of several hours, with periodic manual stirring, after which time it is suitably filtered using a Buchner funnel in order to remove any excess catalyst/solvent. Other impregnation techniques such as the incipient wetness technique can also be used.

The wet supported catalyst thus formed is then suitably placed in an oven at elevated temperature for several hours to dry, after which time it is allowed to cool to ambient temperature in a desiccator. The weight of the catalyst on drying, the weight of the support used and the weight of the catalyst on support is obtained by deducting the latter from the former from which the catalyst loading in g/litre can be determined. This catalyst (measured by weight) is then used in the appropriate process such as eg the olefin hydration process.

The amount of amino compound incorporated in the catalyst composition is suitably in the range from 0.01 to 16% w/w, preferably from 0.1 to 10% w/w based on the weight of the acid catalyst.

The amount of acid catalyst on the support is suitably in the range from 5 to 60% w/w, preferably from 20 to 50% w/w based on the total weight of the acid catalyst and the support.

The catalyst composition so formed may also be further modified by the addition of other acidic components thereto in order to optimise the catalytic activity thereof.

The catalyst compositions of the present invention may be used in a number of catalysed processes such as eg hydration of olefins, polymerisation of olefins, oligomerisation of olefins, and alkylation of hydrocarbons, especially aromatic hydrocarbons.

The catalyst composition of the present invention may also be used in a) alkylation reactions, for example, for the alkylation of cumene, ethylbenzene and aromatic compounds; b) dimerisation reactions, for example, for the dimerisation of olefins; and/or c) oligomerisation reaction, for example, for the oligomerisation of propylene.

According to a further embodiment, the present invention is a process for hydrating olefins to the corresponding alcohols in the vapour phase in the presence of a catalyst composition comprising an acid catalyst supported on a carrier, characterised in that the catalyst composition comprises in addition an amino compound.

The olefin hydration process is suitably carried out using the following reaction conditions:

a. the mole ratio of water to olefin passing through the reactor is suitably in the range from 0.1–3.0, preferably 0.1–1.0 b. the gas hourly space velocity (GHSV) of the water/olefin mixture is suitably from 0.010 to 0.25 g/min/cm$^3$ of the catalyst composition, preferably from 0.03–0.10 g/min/cm$^3$ of the catalyst composition.

c. the catalyst concentration is from 5 to 40% w/w based on the total weight of the catalyst composition, preferably from 10–30% w/w of the total weight of the catalyst composition.

The olefin hydration reaction is carried out at a temperature from 150–350° C. Within this temperature range, the hydration of ethylene to ethanol is suitably carried out at a temperature in the range from its dew point to 350° C., eg 225–320° C. and is preferably from 230–300° C.; the hydration of propylene to isopropanol is suitably carried out at a temperature in the range from its dew point to 250° C., eg 160–225° C. and is preferably from 180–210° C.

The olefins to be hydrated are suitably ethylene or propylene and the corresponding alcohols formed are suitably ethanol and isopropanol respectively. These olefins may be used pure or as a mixture of olefins to generate a corresponding mixture of alcohols. Thus mixed hydrocarbon feedstocks emerging from eg a refinery such as from a fluid catalytic cracking process and comprising a mixture of C2 and C3 saturated and unsaturated hydrocarbons can be used for this purpose. The process is carried out in the vapour phase, ie both the olefin and water are in the vapour phase over the catalyst composition, apart from a small proportion of each gaseous reactant which dissolves in the catalyst composition. The hydration reaction is believed to occur between such dissolved reactants. Ethers corresponding to the olefin are formed as by-products during the reaction.

The hydration reaction is carried out by placing the catalyst composition in a reactor, sealing the reactor and then heating the catalyst composition to the reaction temperature. The catalyst composition is heated to a temperature of between 170 and 300° C. depending upon the end product desired- For instance, if the end product is ethanol from ethylene, the catalyst composition is suitably heated to 225 to 320° C., preferably, 230–300° C. On the other hand, if the end product is iso-propanol from propylene, the catalyst composition is suitably heated to 160–225° C., preferably, 180–210° C. When the catalyst composition has attained the desired temperature a charge of the olefin and water in the vapour state is passed through the reactor. The mole ratio of water to olefin passing through the reactor is suitably in the range from 0.1 to 3.0, preferably from 0.1 to 1.0, more preferably from 0.25–0.45. Within this range the ratio of water to ethylene during the production of ethanol is suitably from 0.1:1 to 5:1, preferably from 0.1:1 to 2.5:1. The space velocity of water vapour/olefin mixture passing through the reactor is subject to slight variations depending upon whether the reactant olefin is ethylene or propylene. For instance, in the case of ethylene, the space velocity of the mixture thereof with water vapour is suitably from 0.010 to 0.100, preferably from 0.020 to 0.050 grammes per minute per cm$^3$ of the catalyst composition. In the case of a mixture of propylene and water vapour, the space velocity is suitably in the from 0.010–0.100, preferably from 0.02–0.07 g/min/cm$^3$ of the catalyst composition.

The hydration reaction is carried out at a pressure ranging from 1000–25000 KPa. Within this range, the hydration of ethylene is suitably carried out at a pressure from 2000 to 24000 KPa, preferably from 3000 to 10000 KPa, whereas the hydration of propylene is suitably carried out at a pressure from 2000–24000 KPa, preferably from 2000–7600 KPa. The activity of the catalyst system was measured by monitoring the total amount of alcohol, ether and unreacted olefin produced over a one-hour period at standard test conditions (specified in the Examples below).

Alcohol and ether production was measured by gas chromatography (see below), whereas unreacted olefin was metered using a wet-type positive displacement flow meter.

Thus, it has now been found that by using the amino compound described herein it is possible not only to increase the space-time-yield (hereafter "STY") of the process but also to prolong the life of the support thereby reducing the frequency with which the support is changed or replaced on a plant.

The present invention is further illustrated with reference to the following Examples:

EXAMPLES

The examples to compare the performance of the organic amine/phosphoric acid/silica catalysts (made as described below in detail) for ethylene hydration were carried out under continuous flow conditions using a copper lined tubular reactor containing 2.5 g of the impregnated catalysts. Preheated ethylene was fed by a mass flow controller and water by a metering pump, passed through a pre-heater prior to entering the catalyst bed.

The temperature of the reactor was controlled within ±1° C. and the pressure, measured at the inlet of the system within ±1 bar. The gaseous effluents were quenched at the reactor outlet in a high pressure separator to 5° C. to condense liquid products and then depressurised to ambient. The off-gases were then passed through a cooling trap of −78° C. to remove any residual liquid products and the gases were accurately metered prior to being vented.

The activity of each of the catalysts was analysed by collecting all condensed products every two hours, and analysing the combined samples for water, ethanol, acetaldehyde and diethyl ether by means of GC analysis. The conversions described are based on water. The phosphoric acid contents of the effluents were analysed through ICP-AES analysis in order to compare the leaching behaviour of the catalysts.

This procedure was used to compare different catalyst compositions in order to establish the superiority of the phosphoric acid catalysts prepared in the presence of small amount of organic amines. The catalyst compositions tested were:Various amount of pure phosphoric acid supported on a silica support Deguss 350 prepared from powdered Aerosil® 200, ex Degussa):

a. 40 wt.% $H_3PO_4$ content b. 50 wt.% $H_3PO_4$ content

Various amounts of dimethyl amine DMA) or trimethyl amine (TMA) added to various amounts of phosphoric acid during the soaking process of a silica support ((Degussa 350 prepared from powdered Aerosil® 200, ex Degussa):

c. 0.6 wt.% DMA, 40 wt.% $H_3PO_4$ content d. 1.0 wt.% DMA, 40 wt.% $H_3PO_4$ content e. 1.5 wt.% DMA, 50 wt.% $H_3PO_4$ content f. 1.0 wt.% TMA, 40 wt.% $H_3PO_4$ content

| Characteristics | Support (ex Dugussa) | Catalyst (a) | Catalyst (b) |
|---|---|---|---|
| $H_3PO_4$-Content (wt. %); ICP-AES | | 38.8 | 49.5 |
| $S_{BET}$ (m²/g) | 205 | n/d | n/d |
| average pore diameter (Å); BJH method | 160 | 190 | 190 |
| c (acid sites, $H_0 \leq -3, 0$) (mmol/g) | 0 | 0.36 | 0.32 | n/d: not determined

Catalyst composition (a and b): $H_3PO_4$ on silica support (Comparative Tests not according to the invention)

5.00 g of silica carrier Degussa 350 prepared from powdered Aerosil® 200, ex Degussa) crushed to 0.4–0.5 mm pellets were charged into a 25 nd flask. 9.41 ml (a) or 14.12 ml (b) of 5.64 mol/l phosphoric acid (ex Merck) were added to the support. The flask was stirred in a rotary evaporator in a water bath at 40° C. for three hours. Then th e rotary evaporator was evacuated to a pressure of 13 mbar and the water bath was heated to reflux. After an hour the flask was allowed to cool down to ambient temperature and pressure was returned to ambient. The catalyst was placed in an oven at 120° C. for 16 hours to dry, after which time it was allowed to cool to ambient temperature in a desiccator.

Catalyst composition (e, d and e): $H_3PO_4$/DMA on silica support (According to the invention)

5.00 g of silica carrier (Degussa 350 prepared from powdered Aerosil® 200, ex Degussa)crushed to 0.4–0.5 mm pellets were charged into a 25 ml flask. 9.51 ml (c), 14.41 ml (d) or 14.55 ml (e) of 5.64 mol/l phosphoric acid (ex Merck) and 126 μl (c), 0.255 μl (d) and 0.387 μl (e) of 40 wt.% solution of DMA (ex BASF) were added to the support. The flask was stirred in a rotary evaporator in a water bath at 40° C. for three hours. Then the rotary evaporator was evacuated to a pressure of 13 mbar and the water bath was heated to reflux. After a hour the flask was allowed to cool down to ambient temperature and pressure was returned to ambient. The catalyst was placed in an oven at 120° C. for 16 hours to dry, after which time it was allowed to cool to ambient temperature in a desiccator.

| Characteristics | Catalyst (c) | Catalyst (d) | Catalyst (e) |
|---|---|---|---|
| $H_3PO_4$-Content (wt. %); ICP-AES | 40.1 | 50.4 | 47.8 |
| Average pore diameter (Å); BJH method | 180 | 200 | 210 |
| c (acid sites, $H_0 \leq -3, 0$) (mmol/g) | — | — | 0.73 |

Catalyst composition (f): $H_3PO_4$/TMA on silica support (According to the invention)

5.00 g of silica carrier ((Degussa 350 prepared from powdered Aerosil®200, ex Degussa) crushed to 0.4–0.5 mm pellets were charged into a 25 ml flask. 9.57 ml (f) of 5.64 mol/l phosphoric acid (ex Merck) and 188μl (f) of a 45 wt.% solution of TMA (ex Fluka) were added to the support. The flask was stirred in a rotary evaporator in a water bath at 40° C. for three hours. Then the rotary evaporator was evacuated to a pressure of 13 mbar and the water bath is heated to reflux. After 1 hour the flask was allowed to cool down to ambient temperature and pressure. The catalyst was placed in an oven at 120° C. for 16 hours to dry, after which time it was allowed to cool to ambient temperature in a desiccator.

The support (ex Degussa) used for the catalysts in the Example (f) had an average pore diameter (A) of 180 as determined by the BJH method (see Article by Barrett, E P, Joyner, L G and Halenda, P P, et al in JACS, 73, 1952, pp 373).

Example 1

The results in Table 1 below compare the water conversion, the ethanol selectivity and the amount of phosphoric acid in the effluents using phosphoric acid/silica based catalyst systems when impregnated with 40% phosphoric acid (a) and with dimethyl amine/40% phosphoric acid. In each case, the temperature used was 300° C., the pressure was 50 bar, the water to ethylene mole ratio was 1:2, the WHSV was 1.6 ml/g catalyst/h. After 8 h time on stream (TOS) the following catalysts performances were observed:

TABLE 1

| Parameter | $H_3PO_4$ impregnated catalyst (a) | $DMA/H_3PO_4$ impregnated catalyst (c) |
| --- | --- | --- |
| Water Conversion (%) | 20.5 | 22.2 |
| Ethanol Selectivity (%) | 99.9 | 99.9 |
| $H_3PO_4$ Concentration (ppm) | 28 | 31 |

Example 2

The results in Table 2 below compare the water conversion, the ethanol selectivity and the amount of phosphoric acid in the effluents using phosphoric acid/silica based catalyst systems when impregnated with 50% phosphoric acid (b) and with various amounts of dimethyl amine/50% phosphoric acid. In these cases, the temperature used was 300° C., the pressure was 50 bar, the water to ethylene mole ratio was 1:2, the WHSV was 1.6 mf/g catalyst/h. After 2, 4 and 6 h time on stream (TOS) the following catalysts performances were observed:

TABLE 2

| Parameter | TOS (h) | $H_3PO_4$ impregnated catalyst (b) | $DMA/H_3PO_4$ impregnated catalyst (d) | $DMA/H_3PO_4$ impregnated catalyst (e) |
| --- | --- | --- | --- | --- |
| Conversion of Water (%) | 2 | 16.3 | 22.1 | 23.4 |
| | 4 | 19.6 | 22.2 | 23.7 |
| | 6 | 19.8 | 21.9 | 23.3 |
| | 8 | 18.5 | 19.3 | 22.7 |
| Selectivity to Ethanol (%) | 2 | 99.1 | 99.0 | 99.0 |
| | 4 | 99.0 | 99.0 | 98.9 |
| | 6 | 98.9 | 98.0 | 97.0 |
| | | 98.9 | 98.9 | 99.2 |
| Concentration $H_3PO_4$ (ppm) | 2 | n/d | n/d | n/d |
| | 4 | 728 | 91 | 47 |
| | | 173 | 21 | 23 |
| | 6 | 254 | 31 | n/d | n/d: not determined

Example 3

The results in Table 3 below compare the water conversion, the ethanol selectivity and the amount of phosphoric acid in the effluents using phosphoric acid/silica based catalyst systems when impregnated with 40% phosphoric acid (a) and with triimethyl amine/40% phosphoric acid. In each case, the temperature used was 300° C., the pressure was 50 bar, the water to ethylene mole ratio was 1:2, the WHSV was 1.6 ml/g catalyst/h. After 8 h time on stream (TOS) the following catalysts performances were observed:

TABLE 3

| Parameter | $H_3PO_4$ impregnated catalyst (a) | $DMA/H_3PO_4$ impregnated catalyst (c) |
| --- | --- | --- |
| Water Conversion (%) | 20.5 | 20.6 |
| Ethanol Selectivity (%) | 99.9 | 99.4 |
| $H_3PO_4$ Concentration (ppm) | 28 | 17 |

We claim:

1. A catalyst composition comprising an acid supported on carrier characterised in that said composition comprises in addition an amino compound wherein said amino compound is non-ionic or cationic.

2. A catalyst composition as claimed in claim 1, wherein said acid catalyst is a phosphoric acid or a heteropolyacid.

3. A catalyst composition as claimed in claim 2, wherein said phosphoric acid catalyst is an ortho-phosphoric acid, a meta-phosphoric acid or a mixture thereof.

4. A catalyst composition as claimed in claim 2, wherein said heteropolyacid catalyst is a polyoxoanion, polyoxometallate or a metal oxide cluster.

5. A catalyst composition as claimed in claim 1, wherein said acid catalyst is 5 to 60 %w/w based on the total weight of the acid catalyst and the carrier.

6. A catalyst composition as claimed in claim 1, wherein said carrier is formed of a siliceous material, clay, titania, zirconia, hafnia, and/or carbon.

7. A catalyst composition as claimed in claim 6, wherein said carrier is a silica carrier.

8. A catalyst composition as claimed in claim 1, wherein said carrier has the following characteristics:

Pore radius (prior to use) of 10–500 Å,

Bulk density of 0.3–0.45 g/ml,

Pore volume (water) of 0.40–1.25 ml/g,

Surface area of 200–750 m$^2$/g,

Average particle size of 0.1–6.0 mm.

9. A catalyst composition as claimed in claim 1, wherein said amino compound is (a) a saturated or unsaturated amine, (b) an open chain, cyclic, alicyclic or exo-cyclic amine, and/or (c) an aliphatic, aromatic or heterocyclic amine, or an ammonium salt thereof.

10. A catalyst composition as claimed in claim 1, wherein said amino compound is 0.01 to 16% w/w based on the weight of the acid catalyst.

* * * * *